United States Patent [19]
Nunberg et al.

[11] Patent Number: 5,422,275
[45] Date of Patent: Jun. 6, 1995

[54] PROTEIN PRODUCTION AT SYNTHETIC START SITE

[75] Inventors: Jack H. Nunberg, Oakland; Annie C. Y. Chang, Palo Alto; Stanley N. Cohen, Portola Valley; Robert T. Schimke, Palo Alto, all of Calif.

[73] Assignee: The Board of Trustees of the Leland Stanford Jr University, Stanford, Calif.

[21] Appl. No.: 163,998

[22] Filed: Dec. 8, 1993

Related U.S. Application Data

[63] Continuation of Ser. No. 324,395, Mar. 16, 1989, abandoned, which is a continuation-in-part of Ser. No. 520,674, Aug. 4, 1983, abandoned, which is a continuation-in-part of Ser. No. 391,886, Nov. 5, 1982, abandoned, which is a continuation-in-part of Ser. No. 198,908, Oct. 21, 1980, abandoned, which is a continuation-in-part of Ser. No. 950,100, Oct. 10, 1978, abandoned.

[51] Int. Cl.⁶ ............................................. C12N 15/70
[52] U.S. Cl. .................. 435/320.1; 435/69.1; 935/29
[58] Field of Search ............... 435/69.1, 172.3, 320.1, 435/252.33; 935/14, 29, 73

[56] References Cited

U.S. PATENT DOCUMENTS 4,237,224 12/1980 Cohen ............................. 435/172.3

OTHER PUBLICATIONS

Alt, et al. (1978) Journal of Biological Chemistry 253:1357. Selective Multiplication of Dihydrofolate Reductase Genes in Methotrexate Resistant Variants of Cultured Murine Cells.

Backman and Ptashne (1978) Cell 13:65–72. Maximizing Gene Expression on a Plasmid Using Recombination In Vitro.

Villa-Komaroff et al, Proc. Natl. Acad. Sci. USA 75:3727 (1978).

*Primary Examiner*—James Martinell
*Attorney, Agent, or Firm*—Bertram I. Rowland

[57] ABSTRACT

Methods and compositions are provided for producing heterologous proteins in a micrcorganism host, particularly bacterium, without fusion to an endogenous protein. Particularly, the heterologous gene may be inserted into a vector comprising an endogenous gene, where the heterologous gene is preceded by a ribosomal binding site. A heterologous enzyme functional in a bacterial host is demonstrated.

1 Claim, No Drawings

PROTEIN PRODUCTION AT SYNTHETIC START SITE

This invention was made with Government support under contract AI07168 awarded by the National Institutes of Health. The Government has certain rights in this invention.

CROSS-REFERENCE TO RELATED APPLICATIONS

This is a continuation of application Ser. No.07/324,395, filed Mar. 16, 1989, now abandoned, which is a continuation-in-part of application Ser. No. 520,674, filed Aug. 4, 1983, now abandoned, which is a continuation-in-part of Ser. No. 391,886, filed Nov. 5, 1982, now abandoned, which is a continuation-in-part of Ser. No. 198,908, filed Oct. 21, 1980, now abandoned, which is a continuation-in-part of Ser. No. 950,100, filed Oct. 10, 1978, now abandoned.

INTRODUCTION

1. Technical Field

The subject invention is in the field of expression of heterologous proteins in microorganisms.

2. Background

With the ability to cleave DNA at specific sequences, ligate DNA, synthesize double-stranded DNA, and clone DNA, the biotechnology revolution was initiated. While the ability to amplify DNA at will provided new opportunities to investigate a wide variety of biological processes at a molecular level, of greater interest was the ability to produce biological products either proteinaceous or non-proteinaceous, which had theretofore been available only from natural sources. It was not clear at the beginning whether one could produce mammalian proteins in a microorganism host, particularly a bacterial host. The codons employed by the different organisms tended to be different, with preferred codons in a prokaryotic host being different from preferred codons in a eukaryotic host and between prokaryotic hosts and eukaryotic hosts. Thus, the codon preference could have affected the ability to express mammalian proteins in microorganisms, unless one could synthesize a coding sequence which would encode the mammalian protein, while providing for the preferred codons of the expression host. Furthermore, as was subsequently discovered, the initial nucleotides downstream from the methionine initiation codon affected the efficiency of expression in the microorganism host. Also, quite surprisingly, mammalian genes included introns, requiring sophisticated splicing mechanisms, where such nucleotide sequences and mechanisms were alien to prokaryotes.

Not only were there uncertainties concerned with the nature of the DNA sequences, but there were additional uncertainties as to the protein products. As determined subsequently, in many cases the protein products produced inclusion bodies, which required isolation and renaturation. Thus, the product initially produced in the microorganism was not functional and required in vitro processing to obtain moderate to low yields of a functional product. In other situations, it was found that a mammalian protein as not isolated. Particularly, where a gene, such as somatostatin, was fused to a short chain of codons of the β-galactosidase gene, no product was obtained. However, when the gene was fused to the β-galactosidase near the 3'-terminus of the gene, the somatostatin sequence was isolatable and based on the construction, could be cleaved from the β-galactosidase protein.

Therefore, there were many uncertainties about whe9ther one could produce heterologous eukaryotic proteins in functional form in a microorganism. The uncertainty involved not only the nucleic acids which would be involved, but whether there would be interactions between the heterologous eukaryotic gene and the regulatory functional groups, whether the protein which was produced would interfere with the viability of the cells, whether the foreign gene would be stable in the microorganism host, and whether the foreign protein produced would be isolatable in a functional form.

Relevant Literature

Chang, et al. *Nature* 275, 617–624 (1978) describes phenotypic expression in *E. coli* of a DNA sequence coding for mouse dihydrofolate reductase. Shine and Dalgarno, *Proc. Natl. Acad. Sci.* USA (1974) 71:1342 describe the 3'-terminal sequence of *E. coli* 16S ribosomal RNA: complementarity to nonsense triplets and ribosomal binding sites. Steitz and Steege *J. Mol. Biol.* (1977) 114:545 and Steege *Proc. Natl. Acad. Sci. USA* (1977) 74:4163 identify sequences on mRNA in the 5' direction from the initiator codon that are complementary to the CCUCC sequence at the 3' end of the 16S ribosomal RNA species proposed to be involved in the binding of mRNA to ribosomes. Komaroff, et al. *Proc. Natl. Acad. Sci.* (1978) 75:3727–3731 describes a bacterial clone synthesizing proinsulin where the recombinant plasmid has a polycytosine tail adjacent an internal codon reciprocal to methionine.

Also of interest is U.S. Pat. No. 4,704,362 which concerns expression of genes comprising a bacterial gene to which the synthetic sequence encoding a mammalian protein is fused.

SUMMARY OF THE INVENTION

Methods and compositions are provided for the production of a foreign protein at least substantially free of heterologous codons. The method provides for joining a DNA sequence encoding a protein from a eukaryotic source, to a ribosomal binding site and a transcriptional initiation regulatory region at the 5'-terminus and a transcriptional termination regulatory region at the 3'-terminus in the direction of transcription. The construct may be introduced into a vector for transformation into a bacterial host for expression of the protein.

DESCRIPTION OF THE SPECIFIC EMBODIMENTS

Methods and compositions are provided comprising transforming DNA foreign to a host and capable of providing protein expression in the host, where the foreign DNA is a gene encoding a heterologous protein joined to the transcriptional and translational regulatory regions recognized by the bacterial host. By appropriate choice of the exogenous gene introduced into the host, an enzyme can be expressed which modifies an endogenous component of the host to produce a nonprotein product of interest.

For transformation, while the foreign DNA may be used by itself, particularly where it provides a basis for selection, the foreign DNA will usually be inserted into a vector, either a vector used for the construction of the foreign DNA and its transcriptional and translational regulatory regions, or a different vector. The vector may be restricted to provide for cohesive ends or may be modified by an oligopolymer, which is complementary to an oligopolymer joined to the foreign DNA.

The modified foreign gene and modified vector are combined and annealed so as to form a structure capable of replication (propagation) in the host strain. The resulting plasmid need not be ligated, ligation apparently occurring in vivo, but may be introduced directly into the unicellular host under transforming conditions. The unicellular host may then be grown, so that the foreign DNA sequence may be expressed, and the DNA structure replicated. Once the structure has been replicated by the unicellular host it need no longer be prepared in vitro.

The term "vector" intends a DNA sequence having an intact or competent replicon and promoter, so that it is capable of replication and transcription to provide mRNA. The vector may be derived from a plasmid, virus or phage which is compatible with the unicellular host.

The foreign DNA structure will usually be a gene which is derived from a source which does not exchange genetic information with the host. The foreign DNA structure may be derived from a prokaryotic or eukaryotic source, usually eukaryotic, may be synthesized, or combinations thereof. The foreign DNA may be obtained from such eukaryotic sources as fungi, filamentous fungi, vertebrates, such as mammals, birds, or the like, reptiles, plants, etc.

Since the plasmid can be used as exemplary of the structure of the recombinant DNA sequence employed for transformation, except that the plasmid and virus are circular, while other DNA sequences derived from phage need not be circular, for the most part the recombinant DNA sequence will be referred to as a plasmid. It should be understood that in referring to a recombinant plasmid, the plasmid is only exemplary and is not limiting. Similarly, as to the foreign DNA sequence, the gene will be used as exemplary of any DNA which provides a useful product and is derived from a source which does not exchange information with the bacterial host.

In referring to the DNA sequences, defining shall intend when transcribed to mRNA, the function of the resulting sequence of ribonucleotides.

The foreign DNA sequence will desirably be joined to a sequence which provides for a phenotypical trait and, as described above, may be modified by the introduction at the 3'termini of an oligopolymer of nucleotides defining a simulated prokaryotic ribosomal binding site, with the terminus being at or adjacent to a nucleotide triplet defining an initiating methionine codon to define a start site. The DNA employed as a vector is also modified at the termini, usually 3', by introducing an oligopolymer having complementary nucleotides to those introduced on the coding strand, so as to serve as cohesive ends for annealing to the modified foreign gene. The modified foreign gene and the vector are combined and annealed providing a DNA structure capable of replication in the host species. The ends may be ligated to form covalent bonds or the DNA structure, e.g., plasmid, may be used directly without ligation in transformation (includes transfection) of a host bacterium. Alternatively, the oligopolymer sequence may be blunt end ligated to the vector and foreign DNA sequence. The bacteria may then be cloned to provide expression of the foreign gene with the protein product being free of proteins from the replicon.

Foreign DNA

The foreign DNA may have one or more DNA sequences, e.g., genes, depending upon the manner in which it was prepared or obtained and the purpose of the transformation. The double stranded DNA may be derived from eukaryotic or prokaryotic cells, viruses and bacteriophage, the source being one which does not normally exchange genetic information with the bacterial host. The fragments employed will generally have molecular weights in the range of about 0.01 to $20 \times 10^6 d$, usually in the range of about 0.1 to $10 \times 10^6 d$.

By introducing one or more exogenous DNA segments into a unicellular organism, the organism will be able to produce polypeptides and proteins ("poly(amino acids)") which the organism could not previously produce. In some instances the poly(amino acids) will have utility in themselves, while in other situations, particularly with enzymes, the enzymatic product(s) will either be useful in itself or useful to produce a desirable product.

One group of poly(amino acids) which are directly useful are hormones. Illustrative hormones include paratnyroid hormones, growth hormone, gonadotropins (FSH, luteinizing hormone, chorionicgonadotropin, and glycoproteins), insulin, ACTH, somatostatin, prolactin, placental lactogen, melanocyte stimulating hormone, thyrotropin, parathyroid hormone, calcitonin, enkephalin, and angiotensin.

Other poly(amino acids) of interest include serum proteins, fibrinogen, prothrombin, thromboplastin, globulin, e.g., gamma-globulins or antibodies, heparin, antihemophilia protein, oxytocin, albumins, actin, myosin, hemoglobin, ferritin, cytochrome, myoglobin, lactoglobulin, histones, avidin, thyroglobulin, interferon, kinins transcortin, and peptide antigens for use in making vaccines.

Where the gene or genes encode for one or more enzymes, the enzymes may be used for fulfilling a wide variety of functions. Included in these functions are nitrogen fixation, production of amino acids, e.g., polyiodohyronine, particularly thyroxine, vitamins, both water and fat soluble vitamins, antimicrobial drugs, chemotherapeutic agents, e.g., antitumor drugs, polypeptides and proteins, e.g., enzymes from apoenzymes and hormones from prohormones, diagnostic reagents, energy producing combinations, e.g., photosynthesis and hydrogen production, prostaglandins, steroids, cardiac glycosides, coenzymes and the like.

The enzyme may be individually useful as agents separate from the cell for commercial applications, e.g., in detergents, synthetic transformations, diagnostic agents and the like. Enzymes are classified by the I.U.B. under the classifications: I. Oxidoreductases; II. Transferases; III. Hydrolases; IV. Lyases; V. Isomerases; and VI. Ligases.

By appropriate choice of one or more genes introduced into a host, the host can be used as a synthetic factory, where an endogenous product either native or foreign to the host, is further chemically modified in one or more steps, by one or more enzymes produced by expression of one or more genes present in a transforming plasmid. The products of primary interest will be other than polypeptides, generally being small molecules of from about 100 to 2000 molecular weight. The substrate for production of the desired product may be a naturally occurring metabolite, a product produced by an exogenous gene introduced into he host, or a compound provided in the nutrient medium which is enzymatically transformed by the enzyme expressed by the foreign gene. For example, the enzyme dihydrofolate reductase may be employed for the reduction of dihydrofolate, produced endogenously, to provide tetratydrofolate.

The subject invention provides for the expression of a foreign gene to produce a foreign enzyme in its active form, where the enzyme is able to survive the alien environment and act upon an organic non-peptide product to produce a non-peptide product of interest. The enzyme is maintained in the cytoplasm and can continuously act upon its substrate to produce the product of interest.

The enzyme is expressed with the same or substantially the same (presence or absence of methionine) N-terminus as the native enzyme. The enzyme having the same amino acid sequence as the native form is able to renature into an active form to be able to effect the enzymatic catalysis of its substrate.

The foreign DNA sequence may be obtained in a wide variety of ways. Conveniently, messenger RNA (mRNA) may be isolated and by employing reverse transcriptase, the DNA can be synthesized. This method has the advantage of providing for a relatively short fragment of DNA, a relatively large source of genetic material, and frequently the presence of the triplet defining the methionine initiator codon. Alternatively, one can synthesize either the mRA or the DNA, either synthesizing the complete sequence de novo or synthesizing fragments and then allowing the fragments to be covalently joined with the appropriate polymerase or ligase enzyme. Another way, with the appropriate chromosomal genetic material, one could employ mechanical shearing or endonuclease cleavage, where the restriction enzyme cleaves at a site adjacent to the nucleotide sequence defining the methionine initiator codon. The desired gee can then be obtained by genomic cloning.

In the event that the nucleotide sequence defining the initiator methionine codon is cleaved from the gene, the appropriate nucleotide bases may be added to provide such sequence, followed by the addition of the bases or oligopolymer to provide the sequence defining the ribosomal binding site or the nucleotides added as a unit. It should be appreciated that while the normal nucleotide triplet on the strand that defines the methionine codon is 5'-dCAT base triplets other than AUG on the mRNA may in particular situations serve to be translated as methionine, e.g., GUG, so that other nucleotide triplets on the sense strand may find use. Desirably, the restriction enzyme employed for isolating the gene from other genetic material will be chosen to provide for the desired nucleotide triplet adjacent the sense strand 3'-terminus.

Vector

In the preparation of the vector or replicon, double-stranded plasmid, viral or phage DNA is cleaved with an appropriate restriction enzyme to provide for an intact replicator locus and system, and promoter. If a plasmid, the plasmid chosen will be capable of replicating in a microorganism, particularly a bacterium, which is susceptible to transformation. Various unicellular microorganisms can be transformed, such as bacteria, fungii, plants, and algae. That is, those unicellular organisms which are capable of being grown in cultures or by fermentation. Bacteria, which are susceptible to transformation, include members of the Enterobacteriaceae, such as strains of *Escherichia coli*; Salmonella; Bacillaceae, such as *Bacillus subtilis*; Pneumococcus; Streptococcus, and *Haemophilus influenzae*.

After cleavage of the plasmid, depending upon the nature of the restriction enzyme, either square ends or slanted ends (cleavage at different but adjacent sites) may be obtained. Restriction enzymes which provide square ends include HaeIII and AluI, and enzymes providing slant ends include PstI and HpaII. As indicated previously, a plasmid need not be used, but rather the DNA may be derived from a virus or phage which is compatible with the bacterial host which is to be transformed. The vital DNA will be treated in the same manner as plasmid DNA for providing the vector.

Where the vector has a gene with the necessary transcriptional and translational regulatory regions, the regulatory regions may be employed with the foreign gene for expression of the foreign gene. Expression can be achieved by insertion of the heterologous gene in the untranslated region downstream from the ribosomal binding site or the initiation methionine codon. Alternatively, the foreign gene may be inserted into the gene of the vector, where the foreign gene is introduced with the ribosomal binding site upstream from the initiation codon of the foreign gene. Desirably, the initiation codon will be out of phase with the initiation codon of the gene into which the foreign gene is inserted. In this manner, the ribosomal binding site will serve for initiation of expression of the foreign gene without fusion to the foreign gene.

Where one employs a simulated ribosomal binding site, such as is produced by poly-G, C tailing, it would be desirable to cleave between the A and G of a CAG sequence. In this manner, one may recreate the endonuclease cleavage site to allow for excision of the foreign gene and introduction of a different foreign gene as desired.

While conveniently, the deoxyribonucleotides defining the simulated ribosomal binding site may be ligated as a unit or added individually to the 3'-termini of the foreign DNA sequence, the same final result of providing for a DNA sequence defining a start site may be achieved in many different ways. For example, a ds DNA segment defining the ribosomal binding site, having the triplet defining the methionine codon, as appropriate, may be blunt or staggered end ligated between the insert (foreign DNA) and the vector.

The need for introduction of the ribosomal binding site to the DNA will be present whenever the genetic material is prepared synthetically, the foreign gene is eukaryotic, or in the preparation or isolation of the gene, the ribosomal binding site has been altered or removed.

In order to provide cohesive ends, the vector may be modified by providing tails complementary to the tails added to the foreign gene. That is, for example, where a poly-d(cytosine) has been conjugated to the 3' ends of the foreign gene, a poly-d(guanosine) will be added to the 3' ends of the vector.

Where poly-G, C tailing is employed or a ribosomal binding site is inserted, the number of members on the coding strand defining the ribosomal binding site will vary depending on whether an identical complementary unit is provided or the binding site is only partially complementary, as in the case of a homopolymer. Usually, there will be on the average at least about three base members, and not more than about 50 base members, more usually from about 8 to 40, and generally from about 10 to 25 base members. Furthermore, on the average, the complementary tail attached to the vector need not be of the same length as the length of the tail added to the coding strand, usually being at least about one-half the number of bases, and may be equal to or slightly greater than the number of bases defining the simulated ribosomal binding site, particularly when the number of bases in the tail attached to the foreign gene is in the low portion of the range.

Conveniently, the bases on the coding strand defining the simulated ribosomal binding site is immediately adjacent the codon complementary to the initiator methionine complementary codon. However, interruption is permissible. The interruption should not exceed about thirty bases, preferably not exceed twenty bases, and more preferably not exceed nine bases. The bases defining the simulated ribosomal binding sine plus the bases intervening between the simulated ribosomal binding site and the bases defining the initiator methionine codon, which together define a start site, may be in phase or out of phase with the gene into which the ribosomal binding site and foreign gene are inserted, preferably out of phase.

Desirably, the vector should have a phenotypical property which allows for selection. Particularly, those genes which provide for survival selection are employed, for example, by providing for resistance to antibiotics or heavy metals or polypeptides, which have bacteriostatic or bacteriocidal functions. Alternatively, a host can be chosen which lacks an appropriate growth factor, which can be supplied by a gene on the vector.

After preparation of the two double stranded DNA sequences, the foreign gene and vector are combined for annealing and/or ligation to provide for a functional recombinant DNA structure. With plasmids, the annealing involves the hydrogen bonding together of the cohesive ends of the vector and the foreign gene to form a circular plasmid which has cleavage sites. The cleavage sites are then normally ligated to form the completely closed and circularized plasmid.

The annealing, and as appropriate, recircularization can be performed in whole or in part in vitro or in vivo. Preferably, the annealing is performed in vitro. The annealing requires an appropriate buffered medium containing the DNA fragments. The temperature employed initially for annealing will be about 40° to 70° C., followed by a period at lower temperature, generally from about 10° to 30° C. The molar ratio of the two segments will generally be in the range of about 1-5:-5-1. The particular temperature for annealing will depend upon the binding strength of the cohesive termini. While 0.5 hr to 2 or more days may be employed for annealing, it is believed that a period of 0.5 to 6 hr may be sufficient. The time employed for the annealing will vary with the temperature employed, the nature of the salt solution, as well as nature of cohesive termini.

The ligation, when in vitro, can be achieved in conventional ways employing DNA ligase. Ligation is conveniently carried out in an aqueous solution (pH6-8) at temperatures in the range of about 5° to 40° C. The concentration of the DNA will generally be from about 10 to 100 μg/ml. A sufficient amount off the DNA ligase or other ligating agent, e.g., T4 ligase, is employed to provide a convenient rate of reaction, generally ranging from about 5 to 50 U/ml. A small amount of a protein, e.g. albumin, may be added at concentrations of about 10 to 200 μg/ml. The ligation with DNA ligase is carried out in the presence of magnesium at about 1-10 mM.

At the completion of the annealing or ligation, the solution may be chilled and is ready for use in transformation.

Various techniques exist for transformation or transfection of a bacterial cell with plasmid DNA. See particularly U.S. Pat. No. 4,237,224, as well as the references cited previously.

The transformed unicellular microorganism may then be cloned in accordance with conventional methods, particularly employing the phenotypical property for selection. The resulting clones are then selected for their capability to produce the functional protein and used for expression of the desired protein in a form free of protein derived from the vector and replication of the plasmid.

The following examples are offered by way of illustration and not by way of limitation.

EXPERIMENTAL (All temperatures not otherwise indicated are in centigrade. The following abbreviations are employed with their indicated meanings: 2ME—2—-mercapoenanol; SSC—saline sodium citrate; DHFR—dihydrofolate reductase; cDNA—complementary DNA; TBE—tris-borate EDTA; PABA—Penassay broth agar.)

EXAMPLE 1

Preparation of pBR332 plasmid with DHFR cDNA insert

DNA complementary to DHFR mRNA was synthesized essentially as described by Buell, et al. *Biol. Chem.* (1978) 253:2471 using arian myeloblastosis virus (AMV) reverse transcriptase and polysomal RNA obtained by indirect immunoprecipitation of DHFR-synthesizing polysomes from methotrexate-resistant AT-3000 S-180 mouse cells (Alt et al. *Biol. Chem.* (1978) 253:1357). The RNA had been estimated to contain DHFR mRNA as 20% of its mRNA. The reaction was carried out in 100 μl (50 mM Tris, pH8.2 at 42°, 140 mM KCl, 10 mM MgCl$_2$, 30 mM 2 ME, 100 μg/ml oligodT (12-18) (Collaborative Research)), 500 μM each deoxynucleotide triphosphate (dNTP) (dCTP was adjusted to ~4 Ci/mm with 32P-dCTP)), 340 μg polysomal RNA (estimated to contain 5 μg polyA-RNA), and 45 units AMV reverse transcriptase. The reaction was incubated at 42° for 30 min and stopped by the addition of 0.25M EDTA pH8.0 to 10 mM.

Approximately 1.4 μg cDNA was synthesized. To the reaction mixture was added *E. coli* tRNA (30 μg), followed by extraction with an equal volume of phenol (saturated with TEN) (2×), followed by ether, before being passed over a Sephadex G-50 fine column (0.7×20 cm) in 10 mM Tris pH 7.4, 2 mM EDTA, 10 mM NaCl (TEN). The void volume was collected and precipitated with 2.5 volumes of ethanol. After centrifugation, the cDNA was dissolved in 200 μl TEN containing 110 mm, NaOH and neared at 70° for 25 min to hydrolyze the RNA, followed by cooling, neutralization with equimolar HCl (buffered with Tris, pH 7.4 to 40 mM) made to 0.4M NaCl and precipitated with ethanol.

After centrifugation, the cDNA was dissolved in 50 μl 5 mM Tris pH 7.4, 0.1 mM EDTA and then used as template for the synthesis of the second strand by *E. coli* DNA polymerase I essentially as described in Seeburg et al. *Nature* (1977) 270:486. (The reaction was carried out at 42° for 10 min in 100 μl (50 mM Tris pH 8.2, 20 mM KCl, 7 mM MgCl$_2$, 10 mM 2 ME, 0.1 mM EDTA) using 1.1 μg cDNA, 10 units *E. coli* DNA polymerase I, and 200 μM of each dNTP with dCTP adjusted to 30 ci/mM as above. Approximately 0.85 μg of the second strand was synthesized. The reaction was stopped and extracted as above before being passed over a Sephadex G-50 fine column (0.5×7 cm) in TEN containing only 0.1 mM EDTA. Column fractions containing the ds cDNA were adjusted to 40 mM NaOAc pH 4.5, 300 mM NaCl, 3 mM Zn(OAc)$_2$ and then treated with *Aspergillus oryzae* S1 nuclease (5 U/ml as described by Wickens, et al. *J. Biol. Chem.* (1978) 253:2483). Digestion was carried out at 37° for 60 min and stopped by the addition of EDTA to 10 mM.

After extraction with phenol and ether (as previously described) and adjusted to 0.3M NaCl, followed by precipitation with ethanol, approximately 1.0 μg ds cDNA was obtained. Aliquots of a) first strand product, b) first strand product after base treatment, c) second strand product and d) second strand product after S1 nuclease treatment were examined on a 1.5% agarose gel under alkaline conditions as described by McDonnel, et al. *J. Mol. Biol.* (1977) 110:119.

Terminal addition of dCTP to the ds cDNA by terminal deoxynucleotide transferase (TdT, Chang and Bollum *J. Biol. Chem.* (1971) 246:909) was carried out by a modification of the Co$^{++}$ procedure (Roychoudhury, et al. *Nuc. Acids Res.* (1976) 3:101). The reaction was performed in 500 μl containing 140 mM cacodylic acid, 30 mM Tris base, 100 mM KOH (final pH 7.6), 0.1 mM dithiothreitol, 150 μm dCTP (adjusted to 8 Ci/mm with $^3$H-dCTP (Amersham)), 1 mM CoCl$_2$ (added to prewarmed reaction mix prior to enzyme addition), approximately 1.0 μg ds cDNA (assuming a number average MW of approximately 600 base pairs, this provides 10 pM 3' termini/ml) and 0.5 μl TdT (2.3×10$^5$ units/ml). The reaction was allowed to proceed at 37° for 10 min before being cooled and sampled to determine incorporation. Approximately 30 dC residues were added per 3' terminus. The reaction was stopped (EDTA so 10 mM), extracted, desalted and precipitated with ethanol as above.

Aliquots of e) second strand product, f) second strand product after S1 nuclease treatment and g) dC-tailed ds cDNA were analyzed on a 1.7% agarose gel in Tris-acetate-NaCl. The dC-tailed ds cDNA was then preparatively electrophoresed on a similar gel and the '1500 base pair' region cut out of the gel and electrophoretically eluted into a dialysis bag as described (see McDonnel, et al. supra). The eluted material was extracted as above, concentrated by lyophilization and precipitated with ethanol. After centrifugation, the '1500 base pair' dC-tailed ds cDNA (approximately 80 ng) was redissolved in 10 mM Tris HCl pH 7.4, o.25 mM EDTA, 100 mM NaCl (annealing buffer).

pBR322 plasmid DNA, isolated as described (Kuperstock and Helinski, *Biochem. Biophys. Res. Commun.* (1973) 54:1451) was digested with a 1.5 fold excess of PstI endonuclease under conditions suggested by the vendor (New England Biolabs) and the linear plasmid DNA was cut out and eluted as described above from a 0.7% agarose gel in TBE (Sharp and Sambrook, *Biochemistry* (1974) 12:3055). The plasmid DNA was 'tailed' with dG residues following the procedures described above. Approximately 15-20 dG residues were added per 3' terminus. Following extraction with phenol and ethanol as previously described, the dG-tailed vector was passed over a Sephadex G-50 file column (0.5×7 cm) in annealing buffer and the void volume was collected. Equimolar amounts of dC-tailed ds cDNA and dG-tailed vector DNA were allotted to anneal essentially as described in Sanger and Coulson, *FEBS Lett.*, (1978) 87:107, except that the vector concentration was kept at 75 ng/ml in the annealing reaction. Circularization was monitored by electron microscopy and was typically about 20-40%. This annealed DNA was used directly for transformation into χ1776 or χ2282.

EXAMPLE 2

Transformation and Cloning with DHFR Containing Plasmid pBR322 plasmid DNA that had been annealed in vitro with dc tailed DHFR cDNA (designated 1°) was introduced into χ1776 or χ2282, using a modification of a previously described transfection procedure (Enea, et al. *J. Mol. Biol.* (1975) 96:495). One ml of an overnight bacterial culture was innoculated into 100 ml of L broth supplemented with diaminopimelic acid (DAP, 50 μg/ml) and (for χ1776 only) thymidine (4 μg/ml). Bacterial cultures were grown until exponential phase at 35° and then harvested by centrifugation at 4°. Cells were washed in 0.3 volume 10 mM NaCl, resuspended in 30 ml freshly prepared MCN buffer (70 mM MnCl$_2$; 40 nM sodium acetate, pH 5.6 and 30 mM calcium chloride) and chilled on ice for 20 min. Cells were collected, resuspended in 1 ml MCN and added in 200 μl aliquots to 50 μl DNA in TEN (10 mM Tris-HCl, pH 7.5; 0.1 mM EDTA, 50 mM NaCl) or MCN buffer. After chilling at 0° for 30 min, reactions were incubated at 27° for 5 min, chilled again for 30 min, and 50 μl samples were plated onto Penassaybroth agar supplemented with DAP, thymidine (for χ1776), and antibiotics as indicated. When χ2282 was used, the selective medium was M9 minimal agar supplemented with 0.5% casamino acids, biotin (2 μg/ml), DAP (50 μg/ml) and trimethoprim (Tp) (2.5-10 μg/ml) plus tetracycline (Tc) or kanamycin (Km) as indicated in Table 1. Plates containing transformants were incubated at 32° and colonies were scored 2 to 3 days after plating. pBR322 plasmid DNA lacking the cDNA insert was used as a control. cDNA preparations labeled as 2° consisted of plasmid DNA isolated from a non-fractionated population of clones that had previously been transformed with chimeric molecules carrying a cDNA insert.

TABLE 1

| | Transforming DNA | | Transformants/ngDNA | |
|---|---|---|---|---|
| Host | Plasmid Vector | Insert | TC 5 μg/ml | TC 10 μg/ml |
| A. χ1776 | pBR322 | none | 4 × 10$^2$ | 2 × 10$^2$ |
| B. χ1776 | pBR322 | cDNA(2°) | 6 × 10$^1$ | 3.2 × 10$^1$ |
| C. χ2282 | pBR322 | cDNA(1°) | 7 × 10$^1$ | — |
| D. χ2282 | pBR322 | cDNA(2°) | 6 × 10$^1$ | — |
| E. χ2282 | pDHFR7 | | 7.5 × 10$^1$ | |

| Tc/Tp 5 μg/ml of each | In Situ hybridization with DHFR cDNA probe (% positive) |
|---|---|
| A. <2 × 10$^{-3}$ | — |
| B. — | 40 |

TABLE 1-continued

| | |
|---|---|
| C. $2 \times 10^0$ | 44 |
| D. $1.3 \times 10^{-1}$ | — |
| E. $2.5 \times 10^1$ | — |

EXAMPLE 3

Detection of Colonies Containing DHFR cDNA Inserts By In Situ Hybridization

Colonies were screened for DHFR sequences using a modification of an in situ hybridization procedure (Grunstein and Hogness, *Proc. Natl. Acad. Sci.* U.S.A. (1975) 72:3961). Tc-resistant colonies were transferred to nitro-cellulose filters (Millipore, HAWG) that had been placed on PABA plates containing Tc (10 μg/ml). (Filters had been washed twice by boiling in H$_2$O and autoclaved prior to placing on plates). After 2-3 days of bacterial growth at 32°, the filter was removed from the plate and placed on a Whatman #3 pad saturated with 0.5N NaOH. After 7', the filter was sequentially transferred to a series of similar pads saturated with 1M Tris pH 7.5 (twice, 7' each); 1.5M NaCl, 0.5M Tris, pH 7.5 (once, 7'); and 0.30M NaCl, 0.03M Nacitrate (2×SSC), (once 7'). After the excess liquid was removed by suction the filter was placed on a pad containing 90% ethanol, dried by suction and backed in vacuo at 80° for 2 hr.

Prior to hybridization, filters were pretreated for 3-6 hr at 65° in hybridization buffer that contained 5×SSC pH 6.1, 0.2% sodium dodecyl sulfate (SDS), 0.02% Ficol 400 (Pharmacia) and 8 μg/ml *E. coli* tRNA. Hybridizations were performed with individual filters in 1.5 ml hybridization buffer containing $2 \times 10^4$ cpm $^{32}$P-labelled purified DHFR cDNA (Alt, et al. *Biol. Chem.* (1978) 253:1357) in a sealed plastic bag at 65° for 24 hr. The filters were then washed in hybridization buffer (once, 60' at 65°); in 5×SSC, pH 6.1 (three times, 60' each at 65°); and in 2×SS, pH 7.4 (twice, 10' at room temperature); air dried, and prepared for autoradiography. A collection of $\chi$1776 colonies were shown to contain a DHFR cDNA insert.

EXAMPLE 4

Inhibitor Analysis of DHFR From Bacterial Cells

Stationary phase cultures of $\chi$2282 expressing trimethoprim resistance were grown in the presence of Tp (1 μg/ml) in minimal medium, washed with isotonic saline, and suspended in 50 mM potassium phosphate buffer pH 7.0 containing 10 mM benzamidine and 10 mM phenyl methyl sulfonyl fluoride (3 volumes buffer to 1 volume cells). The suspension was sonicated and centrifuged at 10,000 rpm for 15 min. The supernatant was centrifuged for 1 hr at 100,000 ×g before being studied. An R$_2$ methotrexate resistant mouse cell extract was prepared. Enzyme activity was measured by the radioactive folic acid assay previously described (Alt, et al. *J. Biol. Chem.* (1976) 251:3063). Protein was determined by the method of Lowry. Approximately 3 units of activity from the $\chi$2282 extract or 5 units from the methotrexate resistant mouse cell extract were incubated with inhibitor for 10 min at 24° before assaying for folate reductase activity; background values were determined by measuring enzyme activity in the presence of 10 mM methotrexate. The results for enzyme activity were closely comparable in the presence of varying concentrations of trimethoprim for the mouse abstracts and $\chi$2282 as evidenced by the amount of enzyme needed to reduce 1 nM of folate in 15 min at 37°.

The subject method provides for the preparation of a functional enzyme free of protein or polypeptide chain from the plasmid vector which might interfere with or significantly change the character of the enzyme from the eukaryotic source. Thus, the subject invention provides a method for introducing a DNA sequence defining a ribosomal binding site adjacent a triplet defining an initiator methionine codon to provide a unit which allows for ribosomal initiation of protein production at the initial site of a DNA sequence foreign to the host. In this manner, the difficult problem of separating the covalently bound vector protein from the foreign protein is avoided.

All publications and patent applications cited in this specification are herein incorporated by reference as if each individual publication or patent application ere specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A DNA plasmid, comprising:
    pBR322 with a poly-GC joined to a cDNA encoding a functional murine dihydrofolate reductase inserted at the PstI site;
    whereby said poly-G,C and cDNA comprise a functional ribosome binding site.

* * * * *